United States Patent [19]

Jousson

[11] Patent Number: 5,277,582
[45] Date of Patent: Jan. 11, 1994

[54] APPARATUS FOR BODILY CARE

[75] Inventor: Jean-Pierre Jousson, Chene-Bourg, Switzerland

[73] Assignee: Les Produits Associes LPA-Broxo S.A., Chene-Bourg, Switzerland

[21] Appl. No.: 963,607

[22] Filed: Oct. 20, 1992

[30] Foreign Application Priority Data

Oct. 29, 1991 [EP] European Pat. Off. ........ 91810836.6

[51] Int. Cl.$^5$ .............................................. A61G 17/02
[52] U.S. Cl. ........................................ 433/80; 128/66
[58] Field of Search ..................... 128/66; 433/80, 81, 433/82, 84, 85

[56] References Cited

U.S. PATENT DOCUMENTS

| 3,966,359 | 6/1976 | Woog ..................... 128/66 |
| 4,111,193 | 9/1978 | Jousson ................. 128/66 |

FOREIGN PATENT DOCUMENTS

| 3347747 | 7/1985 | Fed. Rep. of Germany . |
| 2255049 | 7/1975 | France . |
| 2326176 | 4/1977 | France . |
| 58-200866 | 3/1984 | Japan . |
| 1042065 | 9/1966 | United Kingdom . |

Primary Examiner—John J. Wilson
Attorney, Agent, or Firm—Kane, Dalsimer, Sullivan, Kurucz, Levy, Eisele & Richard

[57] ABSTRACT

The apparatus for bodily care, in particular for massaging the gums and cleaning the teeth, by means of a jet of liquid pulsed by a piston pump, comprises a working chamber (4) connected to an outlet conduit (5), in which chamber the piston (6) is driven with reciprocating movements by an electric motor, an admission chamber (2) connected to an admission conduit (3) and an admission valve (9) arranged in the communication opening between the admission (2) and working (4) chambers, and a reservoir of liquid (12) connected to the admission conduit for feeding a spraying nozzle (17) connected to the outlet conduit (5). The movable part (9a, 9b) of the admission valve (9) is accommodated freely and easily movable without any stress.

5 Claims, 2 Drawing Sheets

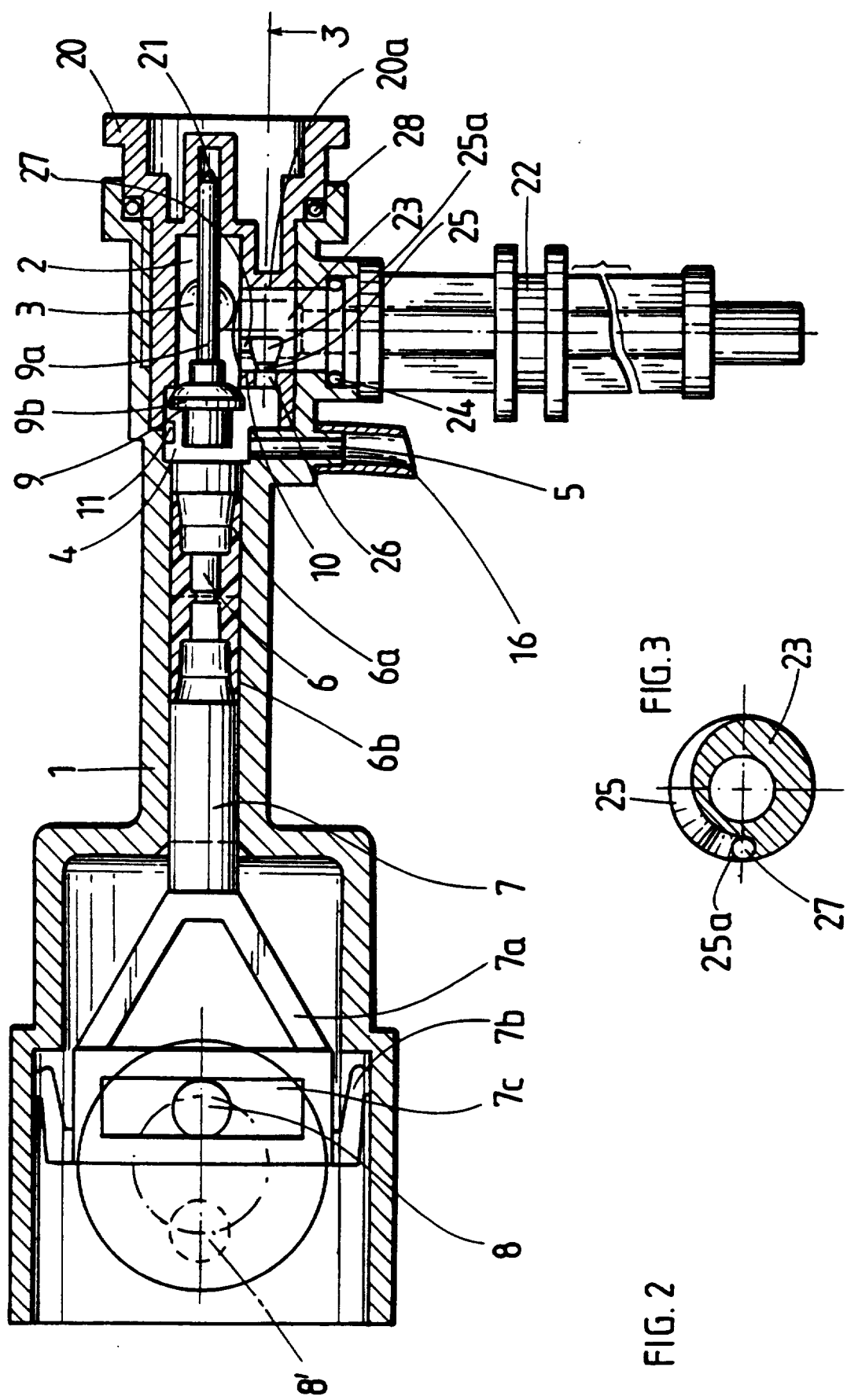

5,277,582

APPARATUS FOR BODILY CARE

FIELD OF THE INVENTION

The invention relates to an apparatus for bodily care, in particular for massaging the gums and cleaning the teeth, by means of a jet of pulsed liquid.

PRIOR ART

According to the patents CH-A-574737 (FR-A 2255049), such an apparatus, without an escape valve between the working chamber of the pump and the outlet conduit leading to the nozzle, is already known. This apparatus comprises an inlet valve which in rest position, when the pump is disengaged, assumes its opening position under the action of a spring which works in the direction of its opening and the force of which is smaller than the closing force acting during the working stroke of the piston of the pump. Moreover, in this known apparatus, the liquid reservoir is connected via the inlet chamber of the pump to a purging shaft which is vertically orientated and serves as a vent.

The first measure mentioned solves the problem of the priming of the pump. In fact, at the time of the engagement of the pump, during the first part of the working stroke of the piston, it is possible that liquid escapes from the working chamber through the inlet valve which is still open and will only be closed, with a given delay, under the action of the pressure of the liquid. In this manner, the starting of the motor under load is avoided, and a reduced starting torque is sufficient to arrive rapidly at the normal functioning speed. The second measure mentioned ensures an immediate delivery of the pump at the time of opening of the valve because the reservoir with the pump, the admission chamber of the pump and the purging shaft constitute a system of communicating vessels which guarantees complete filling of the inlet chamber as soon as the filled reservoir is connected to the inlet pipe of the pump; the air can thus escape completely from the inlet chamber via the purging shaft, the height of the liquid then assuming the same level there as in the reservoir.

However, experience has shown that the purging shaft has a number of disadvantages because it favors the presence of air in the pump. Furthermore, the spring of the valve reduces the capacity because a part of each working stroke of the piston serves first to close the valve counter to the action of the spring before producing the pulsation of liquid towards the nozzle. Moreover, the spring of the valve and the purging shaft are two components which make the assembly of the apparatus slightly complicated and increase the costs of production.

SUMMARY OF THE INVENTION

The aim of the present invention is to produce an apparatus of the type mentioned of simpler construction while ensuring immediate delivery of the pump.

By virtue of the great mobility of the movable part of the valve, the latter follows the movement of the piston virtually without any delay; this means that the valve will be opened immediately when the piston begins a suction stroke and that it will be closed immediately when the piston begins its working stroke, and this irrespectively of whether the working chamber is filled with water or still contains air when the apparatus is set in operation. If air remains, it will in this manner be expelled very rapidly through the outlet conduit of the nozzle, without the need for a purging shaft. In other words, in the presence of air, the pump works effectively as an air pump until this air has been completely eliminated and then begins to pump the liquid by pulsations. By eliminating the purging shaft, the internal space of the pump is only connected to the ambient air through the reservoir and the nozzle and the dead volumes of this shaft are avoided.

Moreover, the minimal space between the piston in its extreme working position and the valve head in its closed position makes it possible essentially to reduce the dead volume in which there may be air.

Preferred embodiments are described in the dependent claims.

BRIEF DESCRIPTION OF THE DRAWINGS

FIG. 2 shows a longitudinal cross-section of the pump.

FIG. 3 is a cross-section along III—III in FIG. 2.

DESCRIPTION OF THE PREFERRED EMBODIMENT(S)

Figure 1:
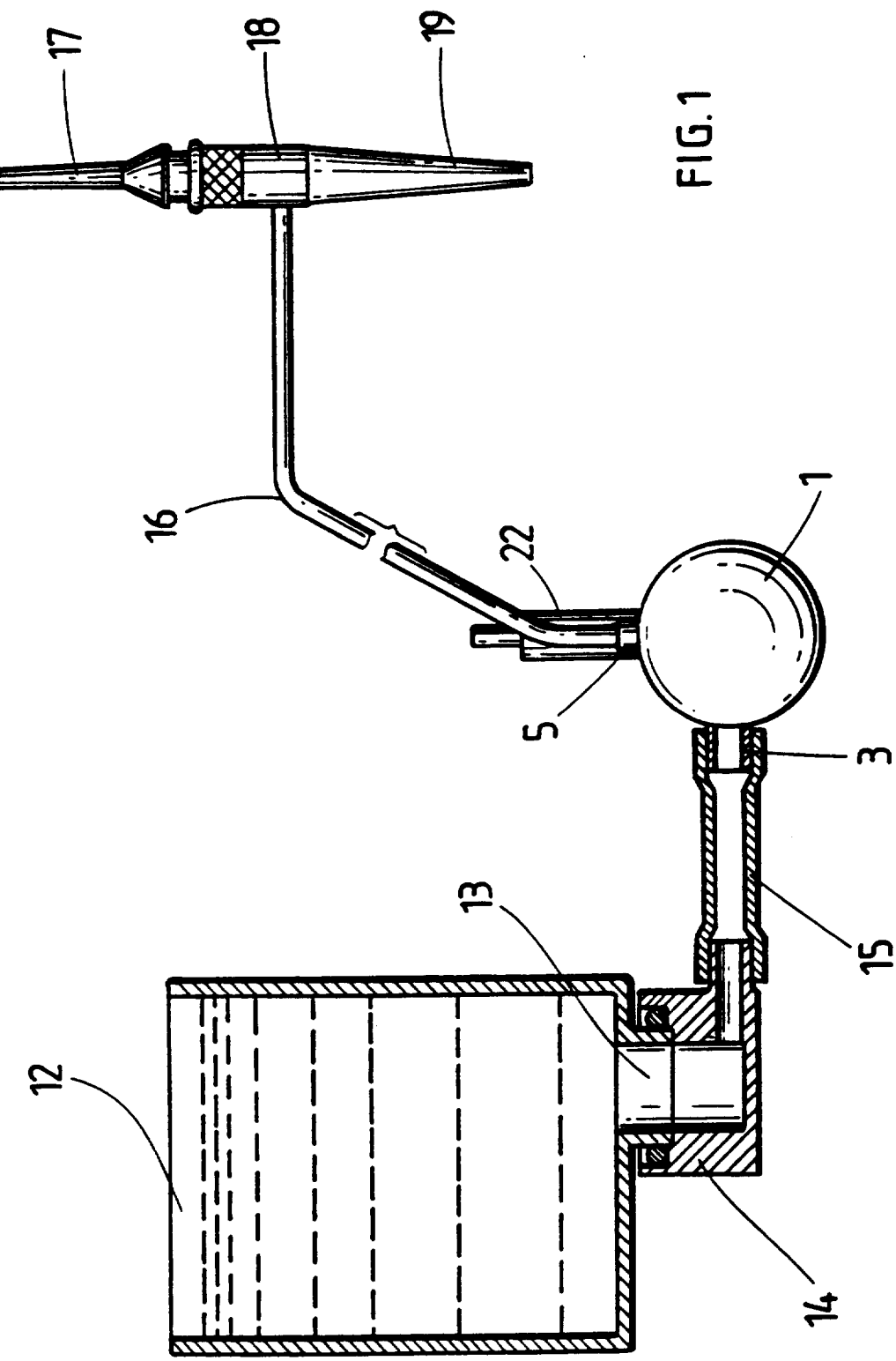
FIG. 1 shows a diagrammatic representation of the apparatus according to the invention in partial cross-section.

According to FIGS. 1 and 2, the apparatus described comprises a pump with its body 1, in which an inlet chamber 2 is connected to an inlet conduit 3, and a working chamber 4 arranged coaxially with the inlet chamber 2 is connected to an outlet conduit 5. Arranged in the working chamber 4 is a piston 6 equipped with a front sealing lip 6a and a rear sealing lip 6b. This piston 6 made of plastic material is fixed on its rod 7 which itself is fixed to a slide 7a equipped with guide shoes 7b. The piston 6 is driven with a reciprocating movement by virtue of an eccentric drive pin 8 passing through a transverse opening 7c of this slide. The eccentric drive pin 8 is fixed eccentrically on the shaft of an electric motor (not shown) and is displaced on the circle drawn in dotted lines in FIG. 2.

FIG. 2 shows the piston 6 and the eccentric pin 8 in the extreme front position while, in the other rear extreme position of the piston (not shown), the eccentric pin is situated in position 8'.

The pump is equipped with an inlet valve 9, the movable part of which comprises a rod 9a and a head 9b and interacts with a seat 10. This valve 9 is orientated in the axis of the chambers of the pump and of the piston 6 and its rod 9a is arranged in the inlet chamber 2 while its hemispherical head 9b penetrates into the working chamber 4. In the position represented in FIG. 2, the valve is closed, its head 9b resting on the seat 10. In the opening position, which is defined by the stops 11 of the internal wall of the working chamber 4, the communication opening between the inlet chamber 2 and the working chamber 4 is completely open. The stroke of the valve 9, limited by a stop 11, is determined in such a manner that its length is as small as possible, in particular between 0.2 and 0.5 mm, preferably 0.35 mm±20%. The movable part 9a, 9b of the valve 9 is mounted without any spring in a free and very movable manner, the end of its rod 9a being accommodated in a cylindrical opening 21 of a piece 20 serving as a valve holder and forming the seat 10. This piece 20 is fixed in the body 1 of the pump, an O-ring 28 being interposed between their respective walls. The movable part 9a, 9b of the valve is produced in a light manner, for example a plastic material like an acetal resin or polyamide, the density of which is 1.2 or less. By virtue of its very light weight, its small size, the actual width being in a practical case only about 18 mm, and of its great mobility, this movable part 9a, 9b can therefore react to the smallest force, or pressure, exerted by the piston in one direction or the other.

According to the preferred example considered, the axes of the valve and of the piston are horizontal in the working position of the apparatus, so that the displacement of the valve is not affected by gravity.

In FIG. 1, a hollow connector 14 can be seen, which is arranged close to the body of the pump 1 and on which a reservoir 12 for the liquid is arranged. This reservoir 12 is equipped with an opening 13 in its lower part, which, when the reservoir is removed from the connector 14, is sealed by any known means (not shown) while, when the reservoir 12 is replaced on its connector 14, said opening 13 is freed and connected to the internal duct of the connector 14 and, via a tube 15, to the inlet conduit 3 of the pump. In the example considered, the connector 14 and the reservoir 12 are situated above the pump. The outlet conduit 5 of the pump is connected via a flexible tube 16 to the handpiece 19 of a spraying nozzle 17, comprising a closing tap 18 which can be actuated by the user. In the closing position of this closing tap 18, the arrival of the liquid at the nozzle 17 is interrupted, while, in the opening position of this tap, the pumped liquid can spray out of the nozzle. The liquid originating from reservoir 12 enters via the tube 15 into the inlet chamber 2 and when the pump is set in operation, bathes the inlet valve 9 perfectly.

When, after a pause, the apparatus, empty or partially filled with liquid, is again set in operation and, to this end, the reservoir 12 filled with water is placed on the connector 14, the inlet chamber 2 of the pump in general contains air, and the water does not reach into the pump, even by gravity. As soon as the motor of the pump is engaged, the pump delivers immediately because the movable part 9a, 9b of the inlet valve 9 follows without delay the movement of the piston 6. As soon as the piston 6 begins its suction stroke, the valve opens, which allows the offtake of the air or of the air/liquid mixture in the working chamber 4. During the next working stroke of the piston, the valve closes rapidly and the air/liquid mixture is pushed towards the outlet conduit. In this manner, the air is rapidly eliminated and the apparatus functions correctly after a number of reciprocating movements of the piston. By virtue of the fact that the stroke of the valve is preferably comprised between 0.2 and 0.5 mm only, the movement of the valve between its closed position and its open position takes place very rapidly.

The space at the front end of the piston 6 in its front extreme position must be as small as possible so as to limit the dead volume to the maximum extent.

In order that the user can regulate the pressure of the liquid expelled from the nozzle 17, an adjustable bypass 26 is provided between the inlet chamber 2 and the working chamber 4, into which it opens next to the valve head 9b. Adjustment is carried out by means of a regulating spindle 22 which is mounted rotationally movably about its axis in a lateral opening 20a provided in the wall of the piece 20 limiting the inlet chamber 2. In the example considered, this regulating spindle 22 extends therefore perpendicularly to the axis of the chambers of the pump.

The part of this regulating spindle 22 which is inserted into the piece 20 is a bushing 23 surrounded by an O-ring 24 and equipped, on a part of its external periphery situated close to its internal end and in front of the opening of the bypass 26, with a circular groove 25. This groove 25 has a variable cross-section starting from a zero cross-section and continuously becoming increasingly greater. The view according to FIG. 2 shows the end 25a of the groove 25 having the greater cross-section, this end being connected to the inlet chamber 2 by an axial opening 27 of the bush 23. If the part of the bushing 23 without a groove is situated in front of the bypass 26, the later is closed. As the regulating spindle 22 with the bushing 23 is turned, a part of the groove 25 having an ever greater cross-section comes into communication with the bypass 26, and the greater the liquid flow through the bypass and returning into the inlet chamber 2. In the example considered, the groove 25 extends preferably over half the periphery of the bushing 23, and therefore there is no longer a groove at the place diametrically opposite its end 25a. This means that the adjustment range for the user is a half-turn of the spindle 22 in order to pass from the closed bypass to the completely open bypass. In the example considered, the variable cross-section is produced by a variable depth (FIG. 3) and also a variable width of the groove 25 which therefore has, in a view developed in a plane, the form of a triangle. This makes it possible to obtain, little by little, a gradual opening of the bypass, starting from point zero.

The invention is not limited to the embodiment which has just been described, but numerous embodiments could be envisaged without leaving the scope of the invention.

I claim:

1. An apparatus for bodily care, in particular for massaging the gums and cleaning the teeth, by means of a jet of liquid pulsed by a piston pump, comprising a piston and a working chamber (4) connected to an outlet conduit (5), in which chamber the piston (6) is driven with reciprocating movements by an electric motor, an inlet chamber (2) connected to an inlet conduit (3) and an inlet valve (9) arranged in the communication opening between the inlet (2) and working (4) chambers, which opening is closed during the working stroke of the piston (6) and opens at the time of the suction stroke, with a reservoir of liquid (12) connected to the inlet conduit (3), and with a spraying nozzle (17) connected to the outlet conduit (5), wherein the movable part (9a, 9b) of the inlet valve (9) is made of light weight material, is accommodated freely without any stress and is capable of being displaced as soon as there is a pressure created by the movement of the piston, such that the inlet vale will open immediately when the piston begins its suction stroke and the inlet valve will be closed immediately when the piston begins its working stroke irrespective of whether the working chamber is filled with liquid or air, the rest position of opening of the inlet valve (9) being defined by a stop (11) which limits the stroke of the valve, the stroke of the valve (9) being between 0.2 and 0.5 mm.

2. The apparatus as claimed in claim 1 wherein the stroke of the valve (9) is 0.35 mm±20%.

3. The apparatus as claimed in claim 1, wherein the valve (9) is arranged coaxial with the piston (6).

4. The apparatus as claimed in claim 1, wherein, in the utilization position of the apparatus, the axis of the valve (9) is orientated horizontally.

5. The apparatus as claimed in claim 1, wherein an adjustable bypass (26) is provided between the inlet (2) and the working (4) chambers, this bypass being covered by the periphery of a rotating cylindrical piece (23) equipped on a part of this periphery with a circular groove (25) of variable cross-section defining, in a given position, the width of the cross-section of the bypass.

* * * * *